United States Patent [19]

Amano et al.

[11] 4,420,631
[45] Dec. 13, 1983

[54] ESTERS OF THE CARBOXYLIC ACID

[75] Inventors: Takehiro Amano, Urawa; Toshihisa Ogawa, Ageo; Kensei Yoshikawa, Kitamoto; Yoshinori Shiobara, Ohmiya; Tatsuhiko Sano, Ohmiya; Yutaka Ohuchi, Ohmiya; Tohru Tanami, Tokyo; Shoichi Ito, Tokyo; Jiro Sawada, Tokyo, all of Japan

[73] Assignee: Taisho Pharmaceutical Co., Ltd., Tokyo, Japan

[21] Appl. No.: 379,632

[22] Filed: May 19, 1982

[51] Int. Cl.$^3$ .............................................. C07L 69/76
[52] U.S. Cl. .................................... 560/104; 424/308
[58] Field of Search ........................................ 560/104

[56] References Cited

U.S. PATENT DOCUMENTS 3,385,886  5/1968  Nicholson et al. .................. 260/515
3,637,767  1/1972  Alvarez ............................... 260/348
4,251,543  2/1981  Amano et al. ...................... 424/317

FOREIGN PATENT DOCUMENTS 2316211  7/1975  France .

Primary Examiner—Paul J. Killos
Attorney, Agent, or Firm—Kenway & Jenney

[57] ABSTRACT

A novel carboxylic acid ester having the following general formula

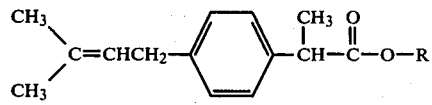

wherein R is alkoxyalkyl having 2 to 6 carbon atoms, cycloalkyl having 5 or 6 carbon atoms, tetrahydrofurfuryl, or alkyl having 1 to 6 carbon atoms optionally substituted with 1 or 2 hydroxyl groups, is a useful anti-inflammatory and analgesic agent.

5 Claims, No Drawings

ESTERS OF THE CARBOXYLIC ACID

BACKGROUND OF THE INVENTION 2-(p-Prenylphenyl)propionic acid (TA-60) described in U.S. Pat. No. 4,251,543 is a very useful anti-inflammatory and analgesic agent as are 2-(p-isobutylphenyl)propionic acid (ibuprofen) and 6-methoxy-α-methyl-2-naphthaleneacetic acid (naproxen).

SUMMARY OF THE INVENTION

As a result of research directed to the above carboxylic acids, we have found that, although esters of ibuprofen and naproxen not only show reduced toxicity but also have reduced anti-inflammatory activity in comparison with the corresponding free acids, to our surprise, only esters of TA-60 maintain high anti-inflammatory activity comparable to TA-60 and show reduced toxicity even when administered at an extremely high dose.

The present invention relates to a novel carboxylic acid ester represented by the following general formula

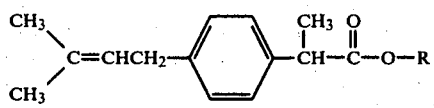  I wherein R is alkoxyalkyl having 2 to 6 carbon atoms, cycloalkyl having 5 or 6 carbon atoms, tetrahydrofurfuryl, alkyl having 1 to 6 carbon atoms and said alkyl substituted with 1 or 2 hydroxyl groups.

In the present specification and claims, unless otherwise noted, the term "alkyl" refers to either straight or branched chain alkyl groups, e.g., primary, secondary and tertiary alkyl groups.

DESCRIPTION AND PREFERRED EMBODIMENTS

Preferred compounds of the present invention are the compounds of formula I wherein R is a straight chain alkyl having 1 to 6 carbon atoms or alkoxyalkyl having 2 to 6 carbon atoms. Most preferred compounds of the present invention are the compounds of formula I wherein R is ethyl or ethoxyethyl.

The compound of formula I may be prepared, for example, by the reaction of the compound of the general formula

RX  II wherein R is defined above, and X is hydroxy, organosulfonyl or halogen, or dialkylsulfate with 2-(p-prenylphenyl)propionic acid or its derivatives. That is, the compound of formula II wherein X is hydroxy may be reacted with (a) 2-(prenylphenyl)propionic acid through dehydrative condensation, (b) 2-(p-prenylphenyl)propionic anhydride, or (c) 2-(p-prenylphenyl)propionyl halide in the presence of a basic condensing reagent such as an organic base (e.g., pyridine, triethylamine and the like) or an inorganic base (e.g., a salt of alkali metal carbonate, alkali metal hydroxide and the like) to give the compound of formula I. The compound of formula II wherein X is organosulfonyl or halogen may be reacted with 2-(p-prenylphenyl)propionic acid in the presence of a basic condensing reagent described above. Dialkylsulfate may be also reacted with 2-(p-prenylphenyl)prioninic acid in the presence of a basic condensing reagent described above. Examples of dialkylsulfates are dimethylsuflate, diethylsulfate and the like.

As stated above, the compounds of the present invention have good anti-inflammatory and analgesic activity with reduced gastrointestinal action at levels comparable to those for 2-(p-prenylphenyl)propionic acid, and show extremely low toxicity, contrary to esters of ibuprofen or naproxen which possess reduced anti-inflammatory activity as well as reduced toxicity in comparison with the corresponding free acids. In addition, since they do not show unpleasant taste, no special technique need be used for their pharmaceutical preparation. Thus, they are useful as anti-inflammatory and analgesic agents in mammals. For these purposes, a compound of the present invention may be administered orally in a conventional dosage form such as tablet, capsule or powder prepared according to conventional pharmaceutical practices. A single dose or preferably 2 to 4 divided daily doses, provided on a basis of about 2–40 mg/kg/day, is appropriate. These compounds may be also administered topically in the range of 0.01 to 10.0% by weight in a conventional cream, ointment or lotion.

The minimum lethal dose of the compounds of the present invention in mice or rats is in excess of 1000 mg/kg of the body weight.

The anti-inflammatory activity of the compounds of the invention was measured by their ability to inhibit granuloma formation in rats according to the following procedure, which is a modification of the procedure described by C. A. Winter et al, J. Pharmacol. Exp. Ther., 141, 369(1963). Ten male rats aged 6 weeks were used in each group. Two paper disks (8 mm diam., 28–29 mg) were implanted subcutaneously on both side of the ventral midline under anesthesia on day 0. Test compounds were given orally to rats once daily for 6 days (from day 0 to day 5). A control group which were implanted with the paper disks received an equivalent volume of the vehicle (5% gum arabic solution). All animals were sacrificed the day after the final dosage, the granuloma was removed from extraneous tissue dried at 70° C. overnight and weighed. Reduction of granulation is expressed as percent decrease over granuloma weight of control group. Body weight gain is also expressed as percent increase over body weight gain of control group.

The results of the tests are presented in the following Table I.

TABLE I

| Cpd. | Dose mg/kg/day | Reduction of granulation (%) | Body weight gain (%) | Incidence of death |
|---|---|---|---|---|
| A | 100 | 23.2 | 115.0 | 0/10 |
|   | 200 | 42.8 | 55.7 | 0/10 |
|   | 300 | 43.6 | 32.0 | 0/10 |
| B | 100 | 22.7 | 113.0 | 0/10 |
|   | 200 | 27.3 | 61.5 | 0/10 |
|   | 300 | 31.9 | 45.9 | 0/10 |
| TA-60 | 100 | 21.2 | 111.9 | 0/10 |
|   | 200 | 38.7 | 23.7 | 0/10 |
|   | 300 | — | — | 6/10 |

Note
Cpd. A: Ethyl 2-(p-prenylphenyl)propionate
Cpd. B: Ethoxyethyl 2-(p-prenylphenyl)propionate The results in Table I show that the compounds of the present invention are almost equal to TA-60 in terms of the anti-inflammatory activity as indicated by the reduction of granulation, and superior to TA-60 in terms of toxicity as indicated by the body weight gain and incidence of death.

In order to further illustrate the present invention, the following examples are provided.

EXAMPLE 1

A mixture of 20.0 g of 2-(p-prenylphenyl)propionic acid and 14.0 g of potassium carbonate in 150 ml of acetone was stirred at room temperature for one hour. To the solution was added dropwise a solution of 15.6 g of diethyl sulfate in 50 ml of acetone with stirring at 25° C. After stirring at room temperature for 3 hours, the mixture was refluxed for an additional one hour with stirring. The precipitate which formed was removed by filtration, and the acetone was evaporated. To the residue was added ice-water, and the mixture was extracted with n-hexane. The extract was washed with water, aqueous sodium bicarbonate and brine successively, and dried over anhydrous magnesium sulfate. The solvent was evaporated to give 18.7 g of ethyl 2-(p-prenylphenyl)propionate. b.p. 108° C./0.15 mmHg, IR $\nu_{max}^{neat}$; 1730 cm$^{-1}$.

EXAMPLE 2

Six grams of powdered potassium hydroxide was dissolved in a mixture of 21.8 g of 2-(p-prenylphenyl)propionic acid in 125 ml of hexamethylphosphoric triamide and 125 ml of ethyl alcohol with stirring at room temperature. To the solution was added 27.4 g of n-butyl bromide and the mixture was stirred at room temperature for 24 hours. The mixture was poured into 500 ml of water and extracted with n-hexane. The extract was washed with 2 N hydrochloric acid, water, 5% aqueous sodium hydroxide and water successively, and dried over anhydrous magnesium sulfate. The solvent was evaporated to give 17.3 g of n-butyl 2-(p-prenylphenyl)propionate. b.p. 131°–133° C./0.15 mmHg, IR $\nu_{max}^{neat}$; 1730 cm$^{-1}$.

EXAMPLE 3

To a solution of 21.8 g of 2-(p-prenylphenyl)propionic acid in 17.6 ml of pyridine and 200 ml of benzene was added dropwise a solution of 7.9 ml of thionyl chloride in 15 ml of benzene with stirring at 4° C. After one hour, 14.8 g of isobutyl alcohol was added. The mixture was stirred at room temperature for one hour and then at 60° C. for 2 hours. After cooling, the solution was washed with water, 2 N hydrochloric acid, water, 5% aqueous sodium hydroxide and water successively, and dried over anhydrous magnesium sulfate. The solvent was evaporated to give 20.1 g of isobutyl 2-(p-prenylphenyl)propionate. b.p. 126°–127° C./0.10 mmHg, IR $\nu_{max}^{neat}$; 1730 cm$^{-1}$.

EXAMPLE 4

To an ice-cooled solution of 26.0 g of 2-(p-prenylphenyl)propionic acid in 200 ml of benzene were added dropwise 15.7 g of thionyl chloride and 10.4 g of pyridine at the same time with stirring over one hour, and then the mixture was stirred at room temperature for 30 minutes. After ice-cooling, to this mixture were added 13.0 g of cyclohexanol and 10.4 g of pyridine. The resulting mixture was stirred for 2 hours at room temperature, and then washed with 1 N hydrochloric acid, water, 5% aqueous sodium hydroxide and water successively, and dried over anhydrous mangesium sulfate. The solvent was evaporated to give 23.5 g of cyclohexyl 2-(p-prenylphenyl)propionate. b.p. 142° C./0.06 mmHg, IR $\nu_{max}^{neat}$; 1730 cm$^{-1}$.

EXAMPLE 5

A mixture of 21.8 g of 2-(p-prenylphenyl)propionic acid, 10.2 g of tetrahydrofurfuryl alcohol and 0.4 g of graphite bisulfate in 100 ml of cyclohexane was stirred at room temperature for 8 hours. The mixture was passed through a column of silica gel, and the solvent was evaporated to give 24.5 g of tetrahydrofurfuryl 2-(p-prenylphenyl)propionate. b.p. 135° C./0.08 mmHg, IR $\nu_{max}^{neat}$; 1730 cm$^{-1}$.

EXAMPLE 6

To an ice-cooled solution of 24.0 g of thionyl chloride and 15.0 g of pyridine in 150 ml of benzene was added dropwise over one hour a solution of 43.6 g of 2-(p-prenylphenyl)propionic acid in 50 ml of benzene with stirring. After stirring at room temperature for 3 hours, this solution was washed with water, dried over anhydrous magnesium sulfate and concentrated. The concentrated solution was added dropwise over one hour to a solution of 92.0 g of glycerine and 15.8 g of pyridine in 150 ml of dimethylformamide at room temperature and stirred for an additional 4 hours. After standing overnight, this solution was poured into 600 ml of water and extracted with ethyl ether. The ethereal solution was washed with water, 5% aqueous sodium hydroxide and water successively, and dried over anhydrous magnesium sulfate. The solvent was evaporated and the residue was purified by a silica gel columnchromatography (n-hexane-chloroform, 4:1) to give 18.0 g of 2,3-dihydroxypropyl 2-(p-prenylphenyl)propionate. IR $\nu_{max}^{neat}$; 1750 cm$^{-1}$.

EXAMPLE 7

Following the procedure of the above Examples and using corresponding starting materials, the 2-(p-prenylphenyl)propionic acid esters shown in Table II were obtained.

Properties of those compounds are listed below together with those of the compounds obtained in Examples 1–6.

TABLE II

General formula

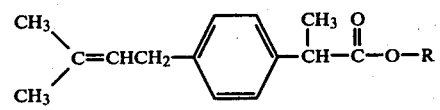

| Examples | Compounds (R) | bp (°C./mmHg) | IR $\nu_{max}^{neat}$ (cm$^{-1}$) |
|---|---|---|---|
| 1 | —C$_2$H$_5$ | 108/0.15 | 1730 |
| 2 | —C$_4$H$_9$ | 131–133/0.15 | 1730 |
| 3 | —iC$_4$H$_9$ | 126–127/0.10 | 1730 |
| 4 | —⟨cyclohexyl⟩ | 142/0.06 | 1730 |
| 5 | —CH$_2$—⟨tetrahydrofurfuryl⟩ | 135/0.08 | 1730 |
| 6 | —CH$_2$CHCH$_2$OH<br>　　　\|<br>　　　OH | — | 1725 |

TABLE II-continued

General formula $$\begin{array}{c}CH_3\\ \phantom{CH}\diagdown\\ \phantom{CH_3}C=CHCH_2-\\ CH_3\diagup\end{array}\!\!-\!\!\bigcirc\!\!-\!\!\begin{array}{c}CH_3\ O\\ |\ \ \ \ \|\\ CH-C-O-R\end{array}$$

| Examples | Compounds (R) | bp (°C./mmHg) | IR $\nu_{max}^{neat}$ (cm$^{-1}$) |
|---|---|---|---|
| 7 | CH$_3$ | 116–120/0.40 | 1735 |
| 7 | —C$_5$H$_{11}$ | 134–135/0.10 | 1730 |
| 7 | —C$_6$H$_{13}$ | 145–146/0.35 | 1730 |
| 7 | —iC$_3$H$_7$ | 120–123/0.40 | 1725 |
| 7 | —iC$_5$H$_{11}$ | 134–137/0.15 | 1730 |
| 7 | CH$_3$\<br>CH$_3$—CCH$_2$—\<br>CH$_3$ | 150–151/0.20 | 1730 |
| 7 | (cyclopentyl) | 120/0.07 | 1730 |
| 7 | —CH$_2$CH$_2$OC$_2$H$_5$ | 136–137/0.20 | 1735 |

TABLE II-continued

General formula $$\begin{array}{c}CH_3\\ \phantom{CH}\diagdown\\ \phantom{CH_3}C=CHCH_2-\\ CH_3\diagup\end{array}\!\!-\!\!\bigcirc\!\!-\!\!\begin{array}{c}CH_3\ O\\ |\ \ \ \ \|\\ CH-C-O-R\end{array}$$

| Examples | Compounds (R) | bp (°C./mmHg) | IR $\nu_{max}^{neat}$ (cm$^{-1}$) |
|---|---|---|---|
| 7 | —CH$_2$CH$_2$OH | 138/0.10 | 1730 |

What is claimed is:

1. A carboxylic acid ester having the following general formula $$\begin{array}{c}CH_3\\ \phantom{CH}\diagdown\\ \phantom{CH_3}C=CHCH_2-\\ CH_3\diagup\end{array}\!\!-\!\!\bigcirc\!\!-\!\!\begin{array}{c}CH_3\ O\\ |\ \ \ \ \|\\ CH-C-O-R\end{array}$$

wherein R is alkoxyalkyl having 2 to 6 carbon atoms, cycloalkyl having 5 or 6 carbon atoms, tetrahydrofurfuryl, alkyl having 1 to 6 carbon atoms or said alkyl substituted with 1 or 2 hydroxy groups.

2. A compound in accordance with claim 1 wherein R is straight chain alkyl having 1 to 6 carbon atoms.

3. A compound in accordance with claim 1 wherein R is alkoxyalkyl having 2 to 6 carbon atoms.

4. A compound in accordance with claim 2 wherein R is ethyl.

5. A compound in accordance with claim 3 wherein R is ethoxyethyl.

* * * * *

UNITED STATES PATENT AND TRADEMARK OFFICE
CERTIFICATE OF CORRECTION

PATENT NO. : 4,420,631

DATED : December 13, 1983

INVENTOR(S) : Amano et al

It is certified that error appears in the above-identified patent and that said Letters Patent is hereby corrected as shown below:

The following information should appear on the face of the patent
--[30] Foreign Application Priority Data
June 5, 1981 (JP) Japan ..... 56-85897--

Col. 1, line 57, delete "2-(prenylphenyl)propionic"
insert --2-(p-prenylphenyl)propionic--

Signed and Sealed this

Eighth Day of May 1984

[SEAL]

Attest:

GERALD J. MOSSINGHOFF

Attesting Officer

Commissioner of Patents and Trademarks